United States Patent
Im

(10) Patent No.: US 8,168,239 B1
(45) Date of Patent: May 1, 2012

(54) METHOD FOR THE PRODUCTION OF DIET FOOD WITH MEDICINAL HERBS

(76) Inventor: Se Kyu Im, Seoul (KR)

( * ) Notice: Subject to any disclaimer, the term of this patent is extended or adjusted under 35 U.S.C. 154(b) by 0 days.

(21) Appl. No.: 13/117,561

(22) Filed: May 27, 2011

(30) Foreign Application Priority Data

Mar. 25, 2011 (KR) .................... 10-2011-0027066

(51) Int. Cl.
| | | |
|---|---|---|
| A61K 36/00 | (2006.01) | |
| A61K 36/234 | (2006.01) | |
| A61K 36/79 | (2006.01) | |
| A61K 36/482 | (2006.01) | |
| A61K 36/752 | (2006.01) | |
| A61K 36/235 | (2006.01) | |
| A61K 36/284 | (2006.01) | |
| A61K 36/481 | (2006.01) | |
| A61K 36/488 | (2006.01) | |
| A61K 36/815 | (2006.01) | |
| A61K 36/254 | (2006.01) | |
| A61K 36/233 | (2006.01) | |
| A61K 36/48 | (2006.01) | |

(52) U.S. Cl. ........ 424/725; 424/736; 424/738; 424/728; 424/776

(58) Field of Classification Search .................. None
See application file for complete search history.

*Primary Examiner* — Qiuwen Mi

(74) *Attorney, Agent, or Firm* — Egbert Law Offices PLLC

(57) ABSTRACT

Disclosed is a method for the production of a diet food with medicinal herbs. According to the method, herbs which have physiological activities suitable for dieting are selected by making reference to various reports and through experimentation. Depending on nutritional and pharmaceutical ingredients responsible for the physiological functions and activities, the herbs are classified into three groups, and combined with each other to form a composition which is extracted in such a manner that as few effective ingredients are lost as possible. The diet food is effective for the prevention and treatment of obesity.

3 Claims, No Drawings

METHOD FOR THE PRODUCTION OF DIET FOOD WITH MEDICINAL HERBS

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to a method for the production of a diet food. More particularly, the present invention relates to a method a method for producing a diet food with medicinal herbs by: preparing a composition comprising 75 parts by weight of at least one medicinal herb selected from the first herb group consisting of *Cnidium monnieri* (L *Cusson*, schisandra fruits, cassia seeds, citrus peel, fennel, *Atractylodes macrocephala*, clove, and red ginseng, all of which require relatively low temperatures for extraction, with a high content of essential oil and high-temperature degradable ingredients and can prevent and suppress obesity by aiding digestion and renal activity, 15 parts by weight of at least one medicinal herb selected from the second group consisting of *Astragalus membranaceus*, *Malva verticillate* L. seeds, plantago seeds, *Wolfiporia cocos*, *Pueraria lobata*, *Polyporus umbellatus*, *Phaseoli* semen, and adlay, all of which promote urination and blood and glucose metabolism and normalize dysmetabolisms, thus being useful in the prevention and treatment of obesity, and 10 parts by weight of at least one medicinal herb selected from the third group consisting of lycium berries, *Acanthopanax sessilflorum Seeman*, and *Bupleurum falcatum* L., all of which are rich in polysaccharides and suppress the accumulation of fat in the body and reduce blood cholesterol levels and lipotropic activity, thus being useful in the treatment of hyperlipidemia and acute and chronic renal failure; extracting the medicinal herb of the first group with an aqueous alcohol solution at a temperature around the boiling point of the alcohol, evaporating the alcohol to give a liquid extract and a solid residue, and separating the liquid extract from the solid residue; extracting both the medicinal herbs of the second and the third groups with an aqueous alcohol solution at a temperature around the boiling point of the alcohol; admixing the solid residue from the first group with the extract from both the second and the third group, heating the admixture at 110~115° C. under elevated pressure to give a liquid extract and a solid residue, and separating the liquid extract from the solid residue; and combining this liquid extract with the liquid extract from the first group, concentrating the combination at room temperature under a reduced pressure, and optionally freeze-drying the concentrated extract and pulverizing it into a powder.

2. Description of Related Art Including Information Disclosed Under 37 CFR 1.97 and 37 CFR 1.98.

Obesity is typically the result of various factors including intake of excessive calories, lack of exercise, genes, etc. In an aspect of physiology, obesity results from endocrinopathy which induces the impairment of digestive and renal functions, abnormal metabolism, and an increase in blood cholesterol and lipid levels. Once lipids enter cells, they may undergo one of two routes, degradation and accumulation. When enzymes involved in degradation pathways are activated, the consumption of energy is promoted by degrading, for example, lipids. On the other hand, when energy is sufficient, the lipids are stored in adipose cells. Thus, the poor efficiency of energy consumption due to an imbalance between energy intake and consumption induces the accumulation of lipids, resulting in obesity.

The accumulation of excessive lipids in the body results in the impairment of physiological functions which leads to the onset of various chronic diseases including diabetes, cardiovascular disorders, lipid metabolism disorders, etc.

Examples of the currently used anti-obesity drugs include the anorexing agents benzphetamine and methamphetamine that stimulate the hypothalamus to restrain appetite, oristat that is a potent inhibitor of pancreatic lipase functioning to prevent the absorption of fats in the diet, and acarbose, which is also an anti-diabetic drug functioning as an α-glucosidase inhibitor. These drugs are effective in the treatment of obesity, but with the concomitant occurrence of side effects such as insomnia, nervousness, increase of blood pressure, gastrointestinal problems, impairment of choleresis, and reduced absorption of lipid-soluble vitamins. In response to the demand for anti-obesity functional foods free of side effects, many products have recently been developed.

Diet foods prepared from natural materials have been introduced.

Korean Patent No. 437699 discloses a herbal extract for the diet which is prepared by immersing a herb mixture of ginseng, *Astragalus membranaceus*, *Imperata cylindrica*, *Pinellia tuber*, adlay, *Ganoderma lucidum*, *Wolfiporia cocos*, lotus leaves and *Lonicera japonica* Thunberg in water for a predetermined period of time and boiling it. However, this extraction method is not effective because the resulting extracts have different nutritional or pharmaceutical ingredients depending on whether water, alcohol, or aqueous alcohol was used as the extraction solvent. Particularly, Pinellia tuber is known to be toxic.

Korean Patent No. 856241 discloses an agar-based diet food composition which is prepared by powdering agar, Garcinia cambogia, indigestible maltodextrin, various cereals, lactic acid bacteria, green tea leaf, L-carnitine, poria, *Astragalus membranaceus*, Houttuynia cordata Thunberg, beans, soy proteins, kale, carrots, angelica, chicory, edible fibers, tangleweed, kuzu vine roots, and pumpkin and mixing the powders in a suitable ratio. However, nowhere is even a method of formulating or forming the composition presented in the patent although the medicinal herbs have different properties and ingredients amongst them. In addition, the diet food composition is nothing but a simple mixture of powdered herbs and thus effects superior to those of individual ingredients cannot be anticipated.

Various other products have been introduced, but their effects have not yet been confirmed.

BRIEF SUMMARY OF THE INVENTION

It is an object of the present invention to provide a method for the production of a diet food with medicinal herbs, which is effective for the prevention and treatment of obesity. In this regard, herbs which have physiological activities suitable for dieting were selected with reference to various reports and through experiments. According to nutritional and pharmaceutical ingredients responsible for the physiological functions and activities, the herbs were classified, and combined with each other to form a composition which was extracted in such a manner that as few effective ingredients were lost as possible.

The above object could be accomplished by a provision of a method for producing a diet food with medicinal herbs, comprising: preparing a composition comprising 75 parts by weight of at least one medicinal herb selected from the first herb group consisting of *Cnidium monnieri* (L.) *Cusson*, schisandra fruits, cassia seeds, citrus peel, fennel, *Atractylodes macrocephala*, clove, and red ginseng, all of which require relatively low temperatures for extraction, with a high content of essential oil and high-temperature degradable ingredients and can prevent and suppress obesity by aiding digestion and renal activity, 15 parts by weight of at least one medicinal herb selected from the second group consisting of *Astragalus membranaceus, Malva verticillate* L. seeds, plantago seeds, *Wolfiporia cocos, Pueraria lobata, Polyporus umbellatus, Phaseoli* semen, and adlay, all of which promote urination and blood and glucose metabolism and normalize dysmetabolisms, thus being useful in the prevention and treatment of obesity, and 10 parts by weight of at least one medicinal herb selected from the third group consisting of lycium berries, *Acanthopanax sessiliflorum Seeman*, and *Bupleurum falcatum* L., all of which are rich in polysaccharides and have the activity of suppressing the accumulation of fats in the body and reducing blood cholesterol levels and lipotropic activity, thus being useful in the treatment of hyperlipidemia and acute and chronic renal failure; extracting the medicinal herb of the first group with an aqueous alcohol solution at a temperature around the boiling point of the alcohol, evaporating the alcohol to give a liquid extract and a solid residue, and separating the liquid extract from the solid residue; extracting both the medicinal herbs of the second and the third group with an aqueous alcohol solution at a temperature around the boiling point of the alcohol; admixing the solid residue from the first group with the extract from both the second and the third group, heating the admixture at 110~115° C. under an elevated pressure to give a liquid extract and a solid residue, and separating the liquid extract from the solid residue; and combining this liquid extract with the liquid extract from the first group, concentrating the combination at room temperature under a reduced pressure, and optionally freeze-drying the concentrated extract and pulverizing it into a powder.

In the method of the production of a diet food, medicinal herbs are extracted with water and alcohol so as to minimize the loss of nutritional and pharmaceutical ingredients. In addition, the diet food of the present invention has the function of inhibiting the activity of lipoprotein lipase (LPL) to suppress the influx of lipids into cells, regulating HSL to promote the degradation of fats of adipose tissues thus to reduce body fat, and activating ACS to promote the catabolic pathway of introduced fatty acids thus to use fatty acids as an energy source. Moreover, the diet food of the present invention, whether in the form of liquid concentrate or powder, suppresses the accumulation of adipose or degenerates lipids in the liver adipose tissues and epididymal adipose tissues, thus showing anti-obesity activity. Further, the diet food of the present invention prevents the accumulation of triglycerides, and thus is expected to reduce the risk of the onset of cardiovascular diseases caused by obesity.

DETAILED DESCRIPTION OF THE INVENTION

The present invention pertains to a method for the production of a diet food with medicinal herbs, comprising:

a first step of preparing a diet herb composition comprising 75 weight parts of at least one medicinal herb selected from the first group consisting of *Cnidium monnieri* (L.) *Cusson*, schisandra fruits, cassia seeds, citrus peel, fennel, *Atractylodes macrocephala*, clove and red ginseng, 15 weight parts of at least medicinal herb selected from the second group consisting of *Astragalus membranaceus, Malva verticillate* L. seeds, plantago seeds, *Wolfiporia cocos, Pueraria lobata, Polyporus umbellatus, Phaseoli* semen, and adlay, and 10 weight parts of at least one medicinal herb selected from the third group consisting of lycium berries, *Acanthopanax sessilflorum Seeman*, and *Bupleurum falcatum* L.;

a second step of immersing 75 weight parts of the medicinal herb of the first group in 450 weight parts of a 50% aqueous alcohol solution at room temperature for 12~24 hours, heating the medicinal herb in the solution at 60~75° C. for 3 hours and then at 78~82° C. to the extent that the alcohol is completely evaporated, to give a liquid extract and a solid residue, and separating the liquid extract from the solid residue;

a third step of immersing 15 weight parts of the medicinal herb of the second group and 10 weight parts of the medicinal herb of the third step in 150 weight parts of a 50% aqueous alcohol solution at room temperature for 12~24 hours and heating the medicinal herb in the solution at 60~75° C. for 3 hours and then at 78~82° C. to the extent that the alcohol completely evaporates, to give a liquid extract and a solid residue, a fourth step of combining the solid residue of the second step with the liquid extract and the solid residue of the third step, heating the combination at 110~115° C. for 60~90 min under a high pressure to give a liquid extract and a solid residue, and separating the liquid extract from the solid residue; and a fifth step of admixing the extract of the fourth step with the extract of the second step and concentrating the admixture at room temperature under a reduced pressure to 20% of the volume thereof.

In another embodiment of the present invention, the extract concentrate may be freeze-dried and pulverized into a powder with a water content less than 3%.

The extract concentrate may be combined with a finely chewable fruit juice while the powder may be formulated, together with a binder such as honey or alginic acid, into pills or may be loaded into gelatin capsules.

The medicinal herbs of the first group require relatively low temperatures for extraction and are rich in essential oils. It is disadvantageous to extract them at high temperatures because they contain aromatic ingredients which are degraded at high temperatures. Thus, they are extracted at less than the boiling point of the alcohol. In herbal medicine, they are widely used as fragrant peptics due to their excellent physiological activity of promoting digestion and bile secretion. Also, they exhibit the activity of improving renal functions and promoting urination and thus are applied to the treatment of pyelonephritis. When abdominally injected into mice, the osthole of *Cnidium monnieri* (L.) *Cusson* suppresses mast cells from degranulation at a rate 56.4~78.6% higher than that of a control. The inhibitory activity against lipase in spleen cells makes it possible to use cloves as an anti-obesity substance.

The medicinal herbs of the second group show various physiological activities. Particularly, they promote urination, blood and glucose metabolism and electrolyte metabolism, and decrease blood cholesterol levels. Upon intake, plantago seeds induce the sense of satiety so that they are used in diets that prevent obesity. *Wolfiporia cocos* shows the activity of normalizing dysmetabolism.

The medicinal herbs of the third group have relatively high polysaccharide content. In addition, *Bupleurum falcatum* L. is useful in the treatment of renal disorders and the normalization of renal functions, and can reduce blood cholesterol levels. The physiological activity of *Bupleurum falcatum* L. was examined. When injected intramuscularly at a dose of 0.3~1 mg/kg for six days with Bupleurum falcatum L. saponin, high-cholesterol diet-fed mice were observed to decrease in blood cholesterol level, serum triglyceride level and serum phospholipid levels to 70~80% of that when injected with a control.

*Acanthopanax sessiliflorum Seeman* is known to be useful for the treatment of hyperlipidemia. In addition, it is lipotropic and helps catalyse the breakdown of lipids during metabolism in the body. Thus, this herb is suitable for use in dieting. (Furthermore, this herb reduces the phagocytosis of abdominal phagocytes and thus is suitable for use in dieting.) Lycium berries are also found to reduce the levels of lipids and cholesterol in the blood and be lipotropic so that it prevents the accumulation of fats in hepatocytes. In addition, this herb was prescribed for renal disorders in the herbal medicine field.

In the present invention, as described above, the medicinal herbs are divided into three groups on the basis of main ingredients, physiological activities and medicinal effects so that they can be treated suitably. Thus, the method of the present invention is designed to effectively extract nutritional and pharmaceutical ingredients from the medicinal herbs in full consideration of the fact that the medicinal herbs of the first group are rich in essential oils and high temperature-degradable ingredients and that ingredients which are dissolved in water or alcohol coexist in the medicinal herbs.

For use in testing its medicinal effect, the diet food (powder) of the present invention was prepared as in Example 1.

A better understanding of the present invention may be obtained through the following examples which are set forth to illustrate, but are not to be construed as limiting the present invention.

Example 1

Each of the medicinal herbs of the first group was used in the same amount to make 75 kg in total. Likewise, each of the medicinal herbs of the second and the third group was used in the same amount to make 15 kg and 10 kg in total, respectively. In 450 kg of a 50% aqueous alcohol solution, 75 kg of the medicinal herb mixture of the first group was immersed for 18 hours at room temperature, followed by thermal treatment at 70° C. for 3 hours and then at 78~82° C. to completely evaporate the alcohol. The resulting liquid extract was separated from the solid residue. Separately, 15 kg of the medicinal herb mixture of the second group and 10 kg of the medicinal herb mixture of the third group were immersed together in 150 kg of an aqueous 50% alcohol solution at room temperature for 18 hours and thermally treated at 70° C. for 3 hours and then at 78~82° C. until the alcohol had completely evaporated. To this mixture was added the solid residue of the first group, followed by thermal treatment at 110~115° C. for 60~90 min under an elevated pressure. The resulting liquid extract was separated from the solid residue and then combined with the liquid extract of the first group. Subsequently, this combination was concentrated under a reduced pressure to 20% of the initial volume and the concentrate was freeze dried to afford a powder with a water content of approximately 3%.

The diet powder was assayed for anti-obesity effect by measuring the activities of the enzymes involved in the fat accumulation and lipid degradation in the body.

1. In vitro Assay

1-A. Selection and Breeding of Experimental Animals for Use as Enzyme Source

Out of 17 9-week-old, male C57BL/6J mice, seven and ten were fed ad libitum with a high fat-free diet and a high fat diet, respectively, for six weeks, along with drinking water. They were bred at a temperature of 21±2° C. and a relative humidity of 50+10±7.5 under a light/dark cycle of 12 hours.

1-B. Preparation of Enzyme Source i. Cytosol.

Each of liver and abdominal adipose tissues was excised in an amount of 3 g and washed with male A (0.25 M sucrose, pH 7.4) to remove blood and foreign substances. This was homogenized in eight volumes of male B (150 mM KCl, 5 mM EDTA, 5 mM MgC12, 10 mM, 2-mercaptoethanol) using a homogenizer at 900 rpm for 5 min. The homogenate was centrifuged at 600×g (Hanil, MF600) for 10 min. The supernatant was mixed with male B and centrifuged at 8,000×g (Beckman, JA-20) for 10 min. After the removal of the pellet, the supernatant was centrifuged again at 105,000×g (Beckman, 70Ti) for 70 min. The resulting supernatant was used as a cytosol fraction.

ii. Treatment of Animal Tissue for Measuring Lipoprotein Lipase (LPL) Activity

Each of liver and abdominal adipose tissue was excised in an amount of 3 g and homogenized at 900 rpm for 5 min in 2 mL of 25 mM $NH_4Cl$ (pH 8.1), followed by centrifugation at 2,000 rpm for 10 min to remove a lipid layer. Again, the supernatant was centrifuged at 12,000 rpm. The resulting supernatant was used as a lipoprotein lipase source.

1-C. Enzyme Activity Assay i. Acyl-CoA Synthetase (ACS)

The activity of Acyl-CoA synthetase (ACS) was measured using the Shimizu method.

ii. Carnitine Acyltransferase (CAT)

measured using the Bergmyer method.

iii. Lipoprotein Lipase measured using the Quinn method.

1-D. Activity of Key Enzymes Involved in Lipid Metabolism

TABLE 1

| Enzyme | Cell | Activity |
|---|---|---|
| Lipoprotein lipase (LPL) | Normal cells | 26.4% inhibited |
|  | Mast cells | 15.5% enhanced |
| Acyl-CoA synthetase (ACS) | Normal cells | 160.5% enhanced |
|  | Mast cells | 421.8% enhanced |
| Carnitine acyltransferase (CAT) | Mast cells | 137.8% enhanced |
| Hormon Sensitive Lipase | Normal cells | 142.8% enhanced |
|  | Mast cells | 115.0% enhanced |

2. In vivo Assay 2-1. In vivo Experiment and Method i. Animal Breed and Diet Preparation The dieting effect of the diet food (sample powder) of the present invention was assayed in vivo. After acclimation for one week, 33 C57BL/6J mice, which are induced to be attacked by obesity and diabetes upon the intake of high-fat diets, were fed for five weeks with a high-fat diet to induce diabetes therein and then for six weeks with a 40% beef tallow-containing AIN-93 diet to induce obesity. Subsequently, the sample powder was provided for the mice as shown in the scheme of Table 2.

TABLE 2

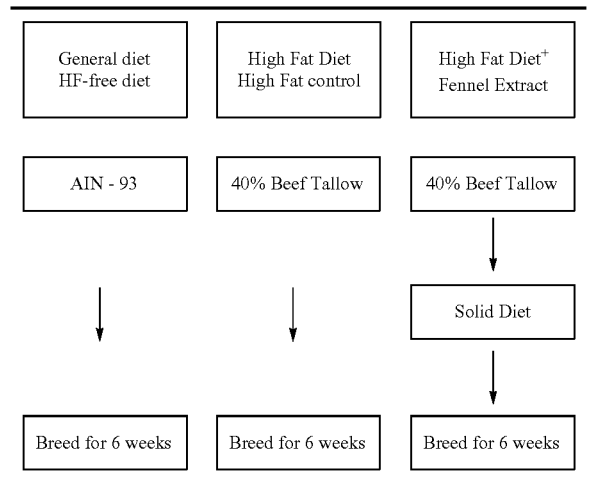

The experimental animals were acclimated for one week and fed ad libitum with diets and drinking water at a temperature of 21±2° C. and a relative humidity of 20±10% under a dark/light cycle of 12 hours.

During the experiment, the amounts of the diet ingested and the body weights of the animals were measured every three days.

ii. Blood Sampling and Measurement of Body Fat

Just after the 6th week at which the diet feed was terminated, the mice were starved and anesthetized before blood samples were taken from the heart. The blood samples were centrifuged at 10,000 rpm for 10 min to separate plasma and blood corpuscles which were then stored at −80° C. until the measurement of blood lipid levels. After the termination of diet feeding, the mice were sacrificed and incised to open the abdomen. Abdominal visceral adipose and epididymal adipose were excised, washed with saline to remove blood and foreign substances, weighed, and stored at −80° C.

ii. Levels of Triglyceride, Total Cholesterol and LDL-Cholesterol in Blood

The levels of total cholesterol (TC), HDL cholesterol (HDL-C) and triglycerides in the blood were measured using commercial kits. LDL cholesterol (LDL-C) levels were calculated using the Friedwald method as follows.

$$LDLc = (TC - HDLc) - \frac{TC}{5}$$

iv. Size of Adipocytes

The epididymal adipose tissue was excised and weighed, and the size and number of the adipocytes were measured. The epididymal adipose was fixed for 48 hours with 10% formalin and sliced into 18 μm-thick sections using a cryo-microtome and stained with Oil-Red-O. Afterwards, the adipocytes were destained with 60% isopropanol and photographed under a microscope equipped with a digital camera. The sizes of the adipocytes were analyzed by measuring the diameters with the aid of a Fluor Chem 8900 image analysis program. The diameters of adipocytes are expressed as fold-induction.

2-2. Assay for Activity of Enzymes Involved in Lipid Metabolism

Measured in the same manner as in the in vitro assay.

2-3. Results of In Vivo Experiments i. Body, Epididymal Adipose Tissue and Liver Tissue Weights

TABLE 3

| Body weight gain/<br>food intake | Liver tissue<br>(g/mouse) | Liver tissue<br>(g/mouse) |
| --- | --- | --- |
| 27.4 | 23.24 | 30.01 | ii. Levels of Lipids and Glucose in Blood

TABLE 4

| Total-<br>cholesterol | HDL-<br>cholesterol | LDL-<br>cholesterol | Triglyceride | Glucose |
| --- | --- | --- | --- | --- |
| 5.43 | 2.15 | 6.00 | 21.52 | 17.07 | iii. Size of Epididymal Adipocyte

Reduced by 22.05% compared to the control fed only with high-fat diet iv. Activity of Key Enzymes Involved in Lipid Metabolism

TABLE 5

| Lipoprotein lipase | Acyl-CoA synthetase |
| --- | --- |
| 32.74% inhibited | 334.3 enhanced |

As described above, the diet food of the present invention, whether in the form of a liquid concentrate or a powder, was found to have the function of inhibiting the activity of lipoprotein lipase (LPL) to suppress the influx of lipids into cells, regulating HSL to promote the degradation of fats of adipose tissues thus to reduce body fat, and activating ACS to promote the catabolic pathway of introduced fatty acids thus to use fatty acids as an energy source. Therefore, the diet food of the present invention is effective for the treatment and prevention of obesity. Although having no significant influences on the activity of ACT, the diet food of the present invention is expected to have anti-obesity effects via other mechanisms as assayed for other enzyme activities and by animal experiments.

According to in vivo experimental results, the diet food of the present invention, whether in the form of a liquid concentrate or a powder, suppressed the accumulation of adipose or degenerated lipids in the liver adipose tissues and epididymal adipose tissues which had gained in weight following a high-fat diet, thus showing anti-obesity activity. In addition, the diet food of the present invention was found to prevent the accumulation of triglycerides as measured by a test for blood lipid levels, and thus is expected to reduce the risk of the onset of cardiovascular diseases caused by obesity.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

I claim:

1. A method for production of a diet food with medicinal herbs, comprising:
    a first step of preparing a diet herb composition comprising medicinal herbs selected from a first, a second and a third group, respectively;
    a second step of immersing 75 weight parts of the medicinal herb of the first group in 450 weight parts of a 50% aqueous alcohol solution at room temperature for 12~24 hours, heating the medicinal herb in the solution at 60-75° C. for 3 hours and then at 78~82° C. to the extent that the alcohol completely evaporates, to give a liquid extract and a solid residue, and separating the liquid extract from the solid residue;
    a third step of immersing 15 weight parts of the medicinal herb of the second group and 10 weight parts of the medicinal herb of the third step in 150 weight parts of a 50% aqueous alcohol solution at room temperature for 12~24 hours and heating the medicinal herb in the solution at 60~75° C. for 3 hours and then at 78~82° C. to the extent that the alcohol is completely evaporated, to give a liquid extract and a solid residue;
    a fourth step of combining the solid residue of the second step with the liquid extract and the solid residue of the third step, heating the combination at 110~115° C. for 60~90 min under a high pressure to give a liquid extract and a solid residue, and separating the liquid extract from the solid residue; and
    a fifth step of admixing the extract of the fourth step with the extract of the second step and concentrating the admixture at room temperature under a reduced pressure to 20% of the volume thereof.

2. The method of claim 1, wherein the diet herb composition comprises 75 weight parts of at least one medicinal herb selected from the first group consisting of *Cnidium monnieri* (L.) *Cusson*, schisandra fruits, cassia seeds, citrus peel, fennel, *Atractylodes macrocephala*, clove and red ginseng, 15 weight parts of at least one medicinal herb selected from the second group consisting of *Astragalus membranaceus, Malva verticillate* L. seeds, plantago seeds, *Wolfiporia cocos, Pueraria lobata, Polyporus umbellatus, Phaseoli semen*, and adlay, and 10 weight parts of at least one medicinal herb selected from the third group consisting of lycium berries, *Acanthopanax sessiliflorum Seeman*, and *Bupleurum falcatum* L.

3. The method of claim 1, further comprising freeze-drying the concentrate resulting from the fifth step in claim 1 to give a powder with a water content of 3% or less.

* * * * *